Figure 1:
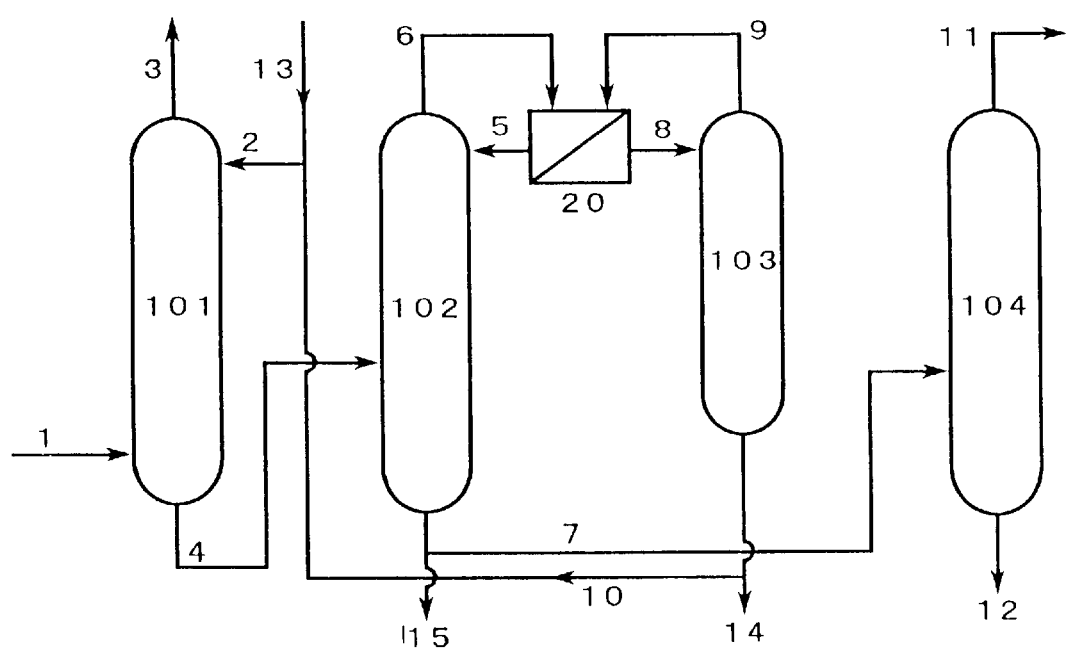

United States Patent
Sakamoto et al.

[11] Patent Number: 6,084,127
[45] Date of Patent: Jul. 4, 2000

[54] METHOD FOR RECOVERING ACRYLIC ACID

[75] Inventors: Kazuhiko Sakamoto; Fumio Shibusawa; Sei Nakahara; Takahiro Takeda; Masatoshi Ueoka, all of Himeji, Japan

[73] Assignee: Nippon Shokubai Co Ltd, Osaka, Japan

[21] Appl. No.: 09/031,068

[22] Filed: Feb. 26, 1998

[30] Foreign Application Priority Data

Feb. 28, 1997 [JP] Japan .................................... 9-046147
May 8, 1997 [JP] Japan .................................... 9-117347

[51] Int. Cl.$^7$ .................................................. C07C 51/42
[52] U.S. Cl. .......................... 562/600; 562/544; 562/545
[58] Field of Search ................................ 562/544, 545, 562/600

[56] References Cited

U.S. PATENT DOCUMENTS

| | | |
|---|---|---|
| 3,432,401 | 3/1969 | Tcherkawsky . |
| 5,315,037 | 5/1994 | Sakamoto et al. .................... 562/545 |

FOREIGN PATENT DOCUMENTS

| | | |
|---|---|---|
| 0551111 | 7/1993 | European Pat. Off. . |
| 46-18967 | 5/1971 | Japan . |
| 46-34691 | 10/1971 | Japan . |
| 63-10691 | 3/1983 | Japan . |
| 5246941 | 9/1993 | Japan . |
| 6-15496 | 3/1994 | Japan . |
| 1120284 | 7/1968 | United Kingdom . |
| 1290725 | 9/1972 | United Kingdom . |
| 2001315A | 1/1979 | United Kingdom . |

*Primary Examiner*—Paul J. Killos
*Assistant Examiner*—Taylor Voh

[57] ABSTRACT

An improved method which enables stable and effective recovery of acrylic acid over a prolonged period is provided, said method comprising contacting an acrylic acid-containing gas obtained upon gas-phase catalytic oxidation of propylene and/or acrolein, with water, whereby collecting the acrylic acid in form of an aqueous solution, introducing said aqueous solution into an azeotropic separation column and distilling it in the presence of an azeotropic solvent to isolate and recover the acrylic acid, in which polymerization of the acrylic acid in the azeotropic separation column is prevented. Said method is characterized by using as the azeotropic solvent either a mixed solvent composed of solvent A (eg., ethyl acrylate, methyl methacrylate, etc.) and solvent B (eg., toluene, heptane, etc.) (first embodiment) or the solvent A alone (second embodiment).

11 Claims, 2 Drawing Sheets

METHOD FOR RECOVERING ACRYLIC ACID

This invention relates to a method for recovering acrylic acid. More particularly, the invention relates to a method comprising contacting an acrylic acid-containing gas, which is obtained in gas-phase catalytic oxidation of propylene and/or acrolein using a molecular oxygen-containing gas, with water whereby collecting said acrylic acid in form an aqueous solution, and distilling the aqueous solution of acrylic acid in the presence of a specific azeotropic solvent, whereby effectively isolating and recovering the acrylic acid.

Production of acrylic acid through gas-phase catalytic oxidation of propylene and/or acrolein has been industrially widely practiced. This method normally consists of an oxidation step to catalytically oxidize propylene and/or acrolein using molecular oxygen in gaseous phase, collection step to collect an acrylic acid-containing gas resulting from the gas-phase catalytic oxidation by contacting said gas with water, and recovery step to isolate and recover acrylic acid from the aqueous solution of the acrylic acid which is obtained in the collection step.

Said acrylic acid-containing gas contains such side-products as acetic acid, formic acid, acetaldehyde, formaldehyde and the like, among which acetic acid is in relatively large quantity. For producing high purity acrylic acid, therefore, acetic acid must be removed. Attempts to remove the acetic acid in the acrylic acid by means of distillation, however, tend to induce polymerization of acrylic acid because of the required high distillation temperature. (Boiling point of acetic acid is 118.1° C.) There is also another problem that the small specific volatility values of acrylic acid and acetic acid render their separation by simple distillation difficult.

Consequently, with the view to isolate and recover high purity acrylic acid from said aqueous acrylic acid solution, that is, to separate acrylic acid from acetic acid and water to recover high purity acrylic acid which is substantially free from acetic acid and water, normally a method of distilling the aqueous acrylic acid solution in an azeotropic separation column in the presence of an azeotropic solvent is adopted. This method comprises, utilizing azeotropic distillation of a three-component system composed of acetic acid-water-solvent, distilling off an azeotropic mixture of acetic acid, water and the solvent from the top of the azeotropic separation column, and recovering acrylic acid from the bottom of the column. The impurities other than acetic acid can be readily removed without relying on azeotropic distillation, because they all have low boiling points.

For example, Japanese Official Patent Gazette, Publication No. Sho 63(1988)-10691 taught a method of such azeotropic distillation using as an azeotropic solvent a hydrocarbon like toluene.

Japanese Official Patent Gazettes, Publication Nos. Sho 46(1971)-34691 and Sho 46(1971)-18967 disclosed the methods using, as azeotropic solvents, butyl acetate, dibutylether, ethyl butyrate, heptane, ethyl methacrylate, propyl acrylate or the like.

Japanese Official Patent Gazette, Publication No. Hei 6(1994)-15496 disclosed a method of carrying out azeotropic distillation using azeotropic solvents such as butyl acetate, methyl isobutyl ketone and the like.

Furthermore, Japanese Official Laid-open Patent Gazette, Laid-open No. Hei 5(1993)-246941 disclosed a method using, as azeotropic solvent, a combination of at least a member selected from a group consisting of diethyl ketone, methyl propyl ketone, methyl isobutyl ketone, methyl-tert-butyl ketone and n-propyl acetate, and at least a member selected from a group consisting of toluene, heptane and methyl cyclohexane.

According to our studies, however, those known methods are subject to various problems as follows.

In the method taught in JP Sho 63-10691, separation of acetic acid is insufficient and necessitates double distillation operations at an azeotropic separation column and an acetic acid separation column for separating acetic acid. Furthermore, because such difficultly water-soluble azeotropic solvent like toluene is present down to the vicinity of bottom of the azeotropic separation column, the liquid in said column comes to be separated into two phases of oleaginous and aqueous layers, which prevent homogeneous dissolution of polymerization inhibitor and the acrylic acid distributed at higher concentration in the aqueous phase is apt to be polymerized.

When those azeotropic solvents which are taught in JP Sho 46-34691 and JP Sho 46-18967 are used, high purity acrylic acid product cannot be obtained with a single distillation operation, because separation of either one of acetic acid, water and solvent is insufficient.

Use of the azeotropic solvents as disclosed in JP Hei 6-15496 gives rise to a problem that separation of the solvent in azeotropic separation column is insufficient and the solvent mixes into the recovered acrylic acid.

Again in a method of recovering high purity acrylic acid with single distillation operation as described in JP-Hei 5-246941 A1, acrylic acid is present at high concentration in the azeotropic separation column, in particular, at the part from the middle plates to upper plates, and hence polymerizing tendency of acrylic acid in the column can by no means be ignored. When polymerizability of acrylic acid in the azeotropic separation column is thus high, acrylic acid polymer accumulates in the column to render continuous running of the azeotropic separation column over a prolonged period difficult.

Accordingly, therefore, an object of the present invention is to solve the problems as above which are encountered in the known art. More specifically, the invention aims at providing a method which comprises, in the occasion of introducing an aqueous acrylic acid solution into an azeotropic separation column and dehydrating by means of azeotropic distillation, preventing polymerization of acrylic acid within said column and distilling acetic acid off from the column top in the form of an azeotropic mixture of acetic acid-water-solvent, whereby recovering from the bottom of said column high purity acrylic acid which is substantially free from acetic acid with high efficiency.

According to our studies, it has been found that above object of the invention can be accomplished by using as the azeotropic solvent, a mixed solvent comprising at least one member selected from the group consisting of ethyl acrylate, methyl methacrylate, vinyl acrylate, allyl acetate, isopropenyl acetate, vinyl propionate and methyl crotonate; and at least one member selected from the group consisting of toluene, heptane, 1-heptene, methylcyclohexane, cycloheptene, cycloheptadiene, cycloheptatriene, 2,4-dimethyl-1,3-pentadiene, methylcyclohexene and methylenecyclohexane; preferably a mixed solvent comprising at least either one of ethyl acrylate and methyl methacrylate, and at least either one of toluene and heptane.

According to the present invention, above object is accomplished by a method comprising collecting an acrylic acid-containing gas, which is obtained upon gas-phase catalytic oxidation of propylene and/or acrolein, in the form of an aqueous acrylic acid solution by contacting said gas with water, and introducing said aqueous acrylic acid solution into an azeotropic separation column and distilling the same in the presence of an azeotropic solvent, whereby isolating and recovering acrylic acid, the method being characterized in that a mixed solvent containing at least one solvent A selected from the group consisting of ethyl acrylate, methyl methacrylate, vinyl acrylate, allyl acetate, isopropenyl acetate, vinyl propionate and methyl crotonate, and at least one solvent B selected from the group consisting of toluene, heptane, 1-heptene, methylcyclohexane, cycloheptene, cycloheptadiene, cycloheptatriene, 2,4-dimethyl-1,3-pentadiene, methylcyclohexene and methylenecyclohexane is used as the azeotropic solvent. Hereinafter this method is referred to as the first embodiment of the present invention.

The characteristic feature of the first embodiment method of this invention resides in the use of the mixed solvent containing above-specified solvent A and solvent B as the azeotropic solvent, in the occasion of introducing an aqueous acrylic acid solution into an azeotropic separation column and distilling the same therein in the presence of an azeotropic solvent to separate and recover the acrylic acid. Use of the specified mixed solvent effectively prevents polymerization of acrylic acid in the azeotropic separation column. Again, as the result of using the specified mixed solvent, it is made possible to distill off acetic acid, water and solvent from the top of the azeotropic separation column and to recover high purity acrylic acid substantially free of acetic acid from the bottom of the column, by only single distillation operation. Hence, according to this embodiment of the present invention, substantially acetic acid-free, high purity acrylic acid can be isolated and recovered upon distilling an aqueous acrylic acid solution in an azeotropic separation column, while preventing polymerization of acrylic acid.

Of the named solvents under group A, ethyl acrylate and methyl methacrylate are preferably used, and of the solvents of group B, toluene and heptane are preferably used.

Thus, as preferred examples of the mixed solvent, the following may be named: ethyl acrylate+toluene, ethyl acrylate+heptane, methyl methacrylate+toluene, methyl methacrylate+heptane, ethyl acrylate+methyl methacrylate+toluene, ethyl acrylate+methyl methacrylate+heptane, and ethyl acrylate+methyl methacrylate+toluene+heptane.

Said ethyl acrylate, methyl methacrylate, toluene and heptane may be those industrially available, which can be used without any further processing.

The blend ratio of solvent A and solvent B ranges 10:90 to 75:25, preferably from 20:80 to 50:50, by weight. When the ratio of solvent A is too high, acetic acid concentration at the bottom of the azeotropic separation column increases, to render it difficult to recover, from aqueous acrylic acid solution, high purity acrylic acid which is substantially free of acetic acid by single distillation operation. Whereas, when the ratio of solvent B is too high, the liquid in the azeotropic separation column separates into oleaginous phase and aqueous phase, and it becomes difficult to prevent polymerization of acrylic acid.

We have also discovered a method which enables recovery of high purity acrylic acid, by use as the azeotropic solvent at least a member of the group consisting of ethyl acrylate, methyl methacrylate, vinyl acrylate, allyl acetate, isopropenyl acetate, vinyl propionate and methyl crotonate, i.e., earlier listed solvent A alone. According to this method, high purity acrylic acid is obtained through two distillation operations, i.e., extracting crude acrylic acid containing acetic acid from bottom of an azeotropic separation column, and then introducing the same into an acetic acid separation column to remove acetic acid therefrom.

Thus, according to the present invention, a method of recovering acrylic acid is provided, which comprises collecting an aqueous acrylic acid solution formed upon contacting an acrylic acid-containing gas obtained from gas-phase catalytic oxidation of propylene and/or acrolein with water, introducing said aqueous solution into an azeotropic separation column and distilling it in the presence of an azeotropic solvent to isolate and recover the acrylic acid, characterized by using as the azeotropic solvent at least one solvent selected from the group consisting of ethyl acrylate, methyl methacrylate, vinyl acrylate, allyl acetate, isopropenyl acetate, vinyl propionate and methyl crotonate. Hereafter this method is referred to as the second embodiment of the present invention.

In the method according to second embodiment of the present invention, ethyl acrylate, methyl methacrylate, vinyl acrylate, allyl acetate, isopropenyl acetate, vinyl propionate and methyl crotonate which are useful as the azeotropic solvent may be those industrially available, which can be used without any further processing. Of those, methyl methacrylate is preferred.

The second embodiment is conveniently used in a process for preparing high purity acrylic acid through the steps of: gas-phase catalytic oxidation step of propylene and/or acrolein using a molecular oxygen-containing gas; collection step of the acrylic acid-containing gas obtained from the gas-phase catalytic oxidation by contacting the same with water; recovery step for isolating and recovering the acrylic acid from the aqueous acrylic acid solution which is obtained in the collection step; and acetic acid-separation step to separate and remove the acetic acid contained as an impurity in the acrylic acid obtained in the recovery step.

Appended FIG. 1 is a flow chart illustrating the first embodiment of the present invention for recovering high purity acrylic acid by single distillation operation. In FIG. 1, the numerals 1–15 denote lines of flow, 101 denotes an acrylic acid collection column, 102 denotes an azeotropic separation column, 103 denotes a solvent recovery column, 104 denotes high-boiling substance separation column and 20, a reservoir.

Hereafter the first embodiment method of the invention following the steps as illustrated in FIG. 1 is explained.

An acrylic acid-containing gas obtained upon gas-phase catalytic oxidation of propylene and/or acrolein using molecular oxygen is introduced into an acrylic acid collection column 101 through line 1, wherein it is contacted with water introduced through line 2. Thus obtained aqueous acrylic acid solution containing acrylic acid and side-products such as acetic acid is withdrawn through line 4. The gas from which the acrylic acid has been collected is discharged through line 3 and recycled to the oxidation reaction step. Occasionally a part of the gas is discarded as gaseous waste, after going through a combustion step. While the water introduced into the acrylic acid collection column 101 through line 2 may be that which is supplied through line 13, preferably the aqueous acetic acid solution discharged from the bottom of a solvent recovery column 103 as later described is used. Then this aqueous acrylic acid solution is introduced into an azeotropic separation column 102, normally without any intervening processing. If necessary, however, it may be first introduced into an acrolein-releasing column (not shown) to be removed of the acrolein dissolved therein and thereafter introduced into said azeotropic separation column 102. In the latter case, the released acrolein is conveniently recovered and recycled into the reaction system.

Into the azeotropic separation column 102, the aqueous acrylic acid solution is fed through line 4, and an azeotropic solvent, through line 5, and distillation is effected. An azeotropic mixture composed of the acetic acid, water and azeotropic solvent is distilled off from the column top through line 6, and acrylic acid which is substantially free of acetic acid is extracted from the column bottom.

Composition of the aqueous acrylic acid solution fed into the azeotropic separation column 102 varies depending on the amount of water supplied to the acrylic acid collection column 101 through line 2, and other operating conditions. Whereas, under conventionally employed acrylic acid-producing conditions, generally the composition consists of: acrylic acid 50–80% by weight; acetic acid 2–5% by weight; and water 20–40% by weight (totalling 100% by weight).

The azeotropic mixture composed substantially of acetic acid, water and azeotropic solvent, which has been distilled off from the top of the azeotropic separation column 102 through line 6, is introduced into a reservoir 20. In the reservoir the mixture is separated into an organic phase composed mainly of the azeotropic solvent and an aqueous phase composed mainly of acetic acid and water. The organic phase is recycled into the azeotropic separation column 102 via line 5, while the aqueous phase is introduced into a solvent-recovery column 103 through line 8. At the solvent-recovery column 103, the azeotropic solvent is distilled off from the column top and returned into the reservoir 20 via line 9, while an aqueous acetic acid solution composed substantially of acetic acid and water is extracted from the bottom of the column 103 through line 14 and discharged off the system. For effective utilization of this aqueous acetic acid solution, it may be recycled into the acrylic acid collecting column 101 through line as earlier indicated, to be contacted with an acrylic acid-containing gas fed through line 1.

The acrylic acid substantially free of acetic acid which is extracted from the bottom of the azeotropic separation column 102, ie., high purity acrylic acid, can be sent to be esterification step via line 15 to be used as a starting material of acrylic acid ester as it is.

For obtaining still higher purity acrylic acid products, the acrylic acid extracted from the bottom of the azeotropic separation column 102 may be introduced into a high-boiling substance-separation column 104 through line 7 and distilled. High-boiling substances such as polymerization inhibitor are extracted from the bottom of said column 104 via line 12, and the higher purity acrylic acid is recovered from the column top via line 11.

The operations at each of the above steps can be conducted under the conditions conventionally employed for this kind of processes. For example, running the azeotropic separation in column 102 under the following conditions (at the time of steady operation), high purity acrylic acid containing no more than 0.05% by weight of acetic acid is obtained.

Operating pressure: 100–200 mmHg
Column top temp.: 45–55° C.
Temperature at aqueous acrylic acid solution supply part (aqueous solution supply plate): 70–90° C.
Temperature at bottom of the column: 100–110° C.
Reflux ratio (total mol number of reflux fluid per unit time/total mol number of distillate per unit time): 1.1–1.6

It is recommendable to add a conventionally used polymerization inhibitor to prevent polymerization of acrylic acid in the azeotropic separation column 102, following conventional practice.

The first embodiment method of the present invention as above, following the flow chart of FIG. 1, to obtain high purity acrylic acid through single distillation operation dispenses with use of an acetic acid-separation column and brings about such advantages that acrylic acid-producing process is simplified and production costs of acrylic acid is markedly reduced.

Figure 2:
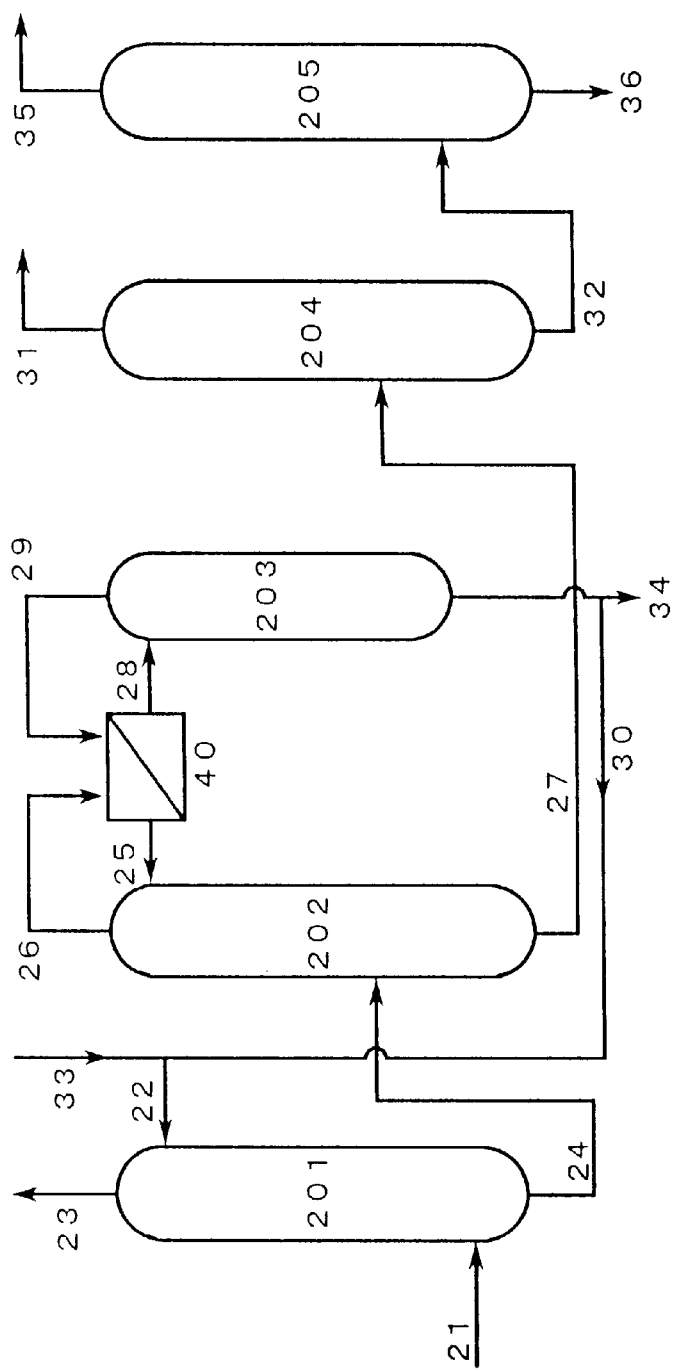

FIG. 2 of appended drawings illustrates the second embodiment method of the present invention in which high purity acrylic acid is recovered through double distillation operations.

In FIG. 2, 21–36 are lines of flow: 201 is an acrylic acid collection column; 202 is an azeotropic separation column; 203 is a solvent recovery column; 204 is an acetic acid separation column; 205 is a high-boiling substance-separation column; and 40 is a reservoir.

Hereafter the second embodiment method of the present invention following the flow chart of FIG. 2 is explained.

An acrylic acid-containing gas obtained upon gas-phase catalytic oxidation of propylene and/or acrolein using a molecular oxygen-containing gas is introduced into an acrylic acid collection column 201 through line 21, wherein it is contacted with water introduced through line 22. Thus obtained aqueous acrylic acid solution containing acrylic acid and side-products such as acetic acid is withdrawn through line 24. The gas from which the acrylic acid has been collected is discharged through line 23 and recycled to the oxidation reaction step. Occasionally a part of the gas is discarded as gaseous waste, after going through a combustion step. While the water introduced into the acrylic acid collection column 201 through line 22 may be that which is supplied through line 33, preferably the waste water discharged from the bottom of a solvent recovery column 203 as later described is used.

Then this aqueous acrylic acid solution is introduced into an azeotropic separation column 202, normally without any intervening processing. If necessary, however, it may be first introduced into an acrolein-releasing column (not shown) to be removed of the acrolein dissolved therein and thereafter introduced into said azeotropic separation column 202. In the latter case, the released acrolein is conveniently recovered and recycled into the reaction system.

Into the azeotropic separation column 202, the aqueous acrylic acid solution is fed through line 24, and an azeotropic solvent, through line 25, and distillation is effected. An azeotropic mixture composed of water and azeotropic solvent is distilled off from the column top through line 26, and acrylic acid containing acetic acid is extracted from the column bottom.

Composition of the aqueous acrylic acid solution fed into the azeotropic separation column 202 varies depending on the amount of water supplied to the acrylic acid collection column 201 through line 22, and other operating conditions. Whereas, under conventionally employed acrylic acid-producing conditions, generally the composition consists of: acrylic acid 50–80% by weight; acetic acid 2–5% by weight; and water 20–40% by weight (totalling 100% by weight).

The azeotropic mixture composed of water and azeotropic solvent, which has been distilled off from the top of the azeotropic separation column 202 through line 26, is introduced into a reservoir 40. In the reservoir the mixture is separated into an organic phase composed mainly of the azeotropic solvent and an aqueous phase composed mainly of water. The organic phase is recycled into the azeotropic separation column 202 via line 25, while the aqueous phase is introduced into a solvent recovery column 203 through line 28. At the solvent recovery column 203, the azeotropic solvent is distilled off from the column top and returned into the reservoir 40 via line 29, while the waste water is extracted from the bottom of the column 203 through line 34 and discharged off the system. For effective utilization, this water may be recycled into the acrylic acid collection column 201 through line 30 as earlier indicated, to be contacted with an acrylic acid-containing gas fed through line 21.

The acetic acid-containing acrylic acid which is extracted from the bottom of the azeotropic separation column 202 is introduced into an acetic acid separation column 204 through line 27 to be removed of the acetic acid. From the top of said column 204 the separated acetic acid is eliminated through line 31, while acrylic acid which contains substantially no acetic acid is recovered from the bottom of the same column. Because the recovered acrylic acid has been highly purified, it can be used as a starting material of acrylic acid esters as it is. Obviously, still higher purity acrylic acid can be obtained by sending said high purity acrylic acid into a high-boiling substance separation column 205 through line 32 and extracting from the bottom of said column 205 high-boiling substance such as polymerization inhibitor through line 36 and recovering the higher purity acrylic acid from the column top through line 35.

For preventing polymer formation in the azeotropic separation column 202, normally a polymerization inhibitor is added. In the present invention, it is also recommendable to add those commonly used polymerization inhibitors.

The operating conditions of the azeotropic separation column 202 in the second embodiment method of the present invention for isolating and recovering acrylic acid through two distilling operations are variable depending on individual acetic acid concentration in crude acrylic acid extracted from the bottom of said column, and hence cannot be uniformly specified. Whereas, by operating the azeotropic separation column under the following conditions (at the time of steady operation), for example, substantially solvent-free acrylic acid containing acetic acid at a concentration of 1 to 9% by weight can be obtained.

Operating pressure: 100–200 mmHg

Column top temp.: 40–50° C.

Temperature at aqueous acrylic acid solution-supply part (aqueous solution supply plate): 45–70° C.

Temperature at bottom of the column: 95–105° C.

Reflux ratio (total mol number of reflux fluid per unit time/total mol number of distillate per unit time): 1.0–1.3.

The distillation of so obtained crude acrylic acid in an acetic acid separation column to obtain high purity acrylic acid is carried out under conventionally employed conditions for this type of distillation.

The second embodiment method of the present invention as above, following the flow chart of FIG. 2, to obtain high purity acrylic acid through two distilling operations, brings about such advantages of excellent solvent separability and effective prevention of undesirable polymer formation.

Hereinafter the invention is explained still more specifically, referring to working examples.

EXAMPLE 1

Acrylic acid was recovered following the steps as illustrated in FIG. 1.

A gaseous mixture obtained by gas-phase catalytic oxidation of propylene using a molecular oxygen-containing gas was led to an acrylic acid collection column 101 and contacted with water. So obtained aqueous solution of acrylic acid was led to an acrolein release column (not shown) where the acrolein contained in said solution was released. The remaining aqueous acrylic acid solution contained 30% by weight of water and 3.0% by weight of acetic acid. The solution was then distilled in an azeotropic separation column 102 equipped with a sieve tray with 50 plates disposed at regular intervals of 147 mm each, a distillation pipe at the column top, a starting material supply pipe at the center and a bottom product-extracting pipe at the bottom part. As the azeotropic solvent, a mixed solvent of methyl methacrylate and toluene (blend ratio: 35:65 by weight) was used. As the polymerization inhibitor, 15 ppm of copper dibutyldithiocarbamate, 22.5 ppm of manganese acetate,. 75 ppm of hydroquinone and 75 ppm of phenothiazine, each to the amount of evaporated acrylic acid vapor, were used. Said manganese acetate was supplied into the column in the form as dissolved in the starting material, through the starting material-supply pipe, and other inhibitors, in the form as dissolved in the reflux fluid, from the column top. Separately, 0.3% by volume to the vapor of evaporated acrylic acid of molecular oxygen was supplied to the bottom part of the column. Here the amount of the evaporated vapor signifies the total volume of the monomer vapor evaporated from the bottom of the column in correspondence to the heat applied from the reboiler of the distillation column.

The operating conditions of the azeotropic separation column 102 at the steady operation time were: column top temperature, 50° C.; column bottom temperature, 105° C.; column top pressure, 160 mmHg, reflux ratio (total mol number of reflux fluid per unit time/total mol number of distillate per unit time), 1.32; and the aqueous acrylic acid solution supply through line 4, 9.3 liters/hour. The aqueous phase passing through line 8 contained 7.6% by weight of acetic acid and 0.6% by weight of acrylic acid. Whereas, the fluid extracted from the bottom of the azeotropic separation column 102 through line 15 contained 96.9% by weight of acrylic acid, 0.03% by weight of acetic acid and 3.10% by weight of other miscellaneous components, while containing no more than the detection limit (1 ppm) of the solvent.

The aqueous phase obtained through line 8 was introduced into the solvent recovery column 103, and from the top of said column the solvent was recovered through line 9, while from the bottom of the column an aqueous acetic acid solution was withdrawn through line 14. Said solution which was composed of 8.1% by weight of acetic acid, 0.64% by weight of acrylic acid and balance of water was recycled into the acrylic acid collection column 101 to be contacted with the gaseous mixture obtained by the gas-phase catalytic oxidation of propylene (i.e., to be used as the collector in place of water).

When the azeotropic separation column 102 was continuously run for about 14 days under the specified conditions, steady operating conditions were constantly obtained. When inside of the column was inspected after suspension of the operation, indication of polymer formation was nil.

COMPARATIVE EXAMPLE 1

Azeotropic distillation of aqueous acrylic acid solution was conducted in identical manner with Example 1, except that methyl methacrylate alone was used as the azeotropic solvent and the reflux ratio was reduced to 1.24.

The aqueous phase at line 8 at steady operation time contained 6.3% by weight of acetic acid and 4.5% by weight of acrylic acid, ie, as much as about 8 times the acrylic acid content in the aqueous phase in Example 1. On the other hand, the fluid extracted from the bottom of the azeotropic separation column 102 through line 15 contained 96.2% by weight of acrylic acid, 0.3% by weight of acetic acid and 3.5% by weight of other miscellaneous components. Thus, its acetic acid content was as high as ten times that of the product of Example 1.

As above, when methyl methacrylate alone was used as the azeotropic solvent, high purity acrylic acid could not be recovered from the azeotropic separation column 102.

COMPARATIVE EXAMPLE 2

Azeotropic distillation of aqueous acrylic acid solution was conducted in identical manner with Example 1, except that a mixed solvent of methyl isobutyl ketone and toluene (blend ratio: 65:35 by weight) was used as the azeotropic solvent and the reflux ratio was increased to 1.42.

The aqueous phase at line 8 at steady operation time contained 6.9% by weight of acetic acid and 0.5% by weight of acrylic acid. Whereas, the fluid extracted from the bottom of the azeotropic separation column 102 through line 15 contained 96.9% by weight of acrylic acid, 0.08% by weight of acetic acid, 0.002% by weight of the solvent and 3.02% by weight of other miscellaneous components.

When the azeotropic separation column 102 was run under the above-stated conditions continuously for about 14 days, stable operation was possible almost throughout, but when the distillation column was dismembered and inspected after the operation was suspended, formation of a minor amount of popcorn polymer in the column was recognized.

EXAMPLE 2

Azeotropic distillation of aqueous acrylic acid solution was conducted in the same manner as in Example 1, except that a mixed solvent of ethyl acrylate and toluene (blend ratio: 35:65 by weight) was used as the azeotropic solvent.

The aqueous phase at line 8 at steady operation time contained 7.3% by weight of acetic acid and 0.5% by weight of acrylic acid. Whereas, the fluid extracted from the bottom of the azeotropic separation column 102 through line 15 contained 97.2% by weight of acrylic acid, 0.03% by weight of acetic acid and 2.80% by weight of other miscellaneous components. Its solvent content was no more than the detection limit (1 ppm).

When the azeotropic separation column 102 was continuously operated for about 14 days under the above conditions, always stable conditions were maintained. When inside of the distillation column was inspected after the operation was suspended, no formation of polymer was observed.

COMPARATIVE EXAMPLE 3

Azeotropic distillation of aqueous acrylic acid solution was conducted in the identical manner with that in Example 1, except that ethyl acrylate alone was used as the azeotropic solvent and the reflux ratio was reduced to 1.24.

The aqueous phase at line 8 at steady operation time contained 6.5% by weight of acetic acid and 4.9% by weight of acrylic acid, ie, as much as about 8 times the acrylic acid content in the aqueous phase in Example 1. On the other hand, the fluid extracted from the bottom of the azeotropic separation column 102 through line 15 contained 96.5% by weight of acrylic acid, 0.3% by weight of acetic acid and 3.2% by weight of other miscellaneous components. Thus, its acetic acid content was as high as ten times that of the product of Example 1.

As above, when ethyl acrylate alone was used as the azeotropic solvent, high purity acrylic acid could not be recovered from the azeotropic separation column 102.

EXAMPLE 3

Azeotropic distillation of aqueous acrylic acid solution was conducted in identical manner with Example 1, except that a mixed solvent of ethyl acrylate and heptane (blend ratio: 35:65 by weight) was used as the azeotropic solvent and the reflux ratio was decreased to 1.24.

The aqueous phase at line 8 at steady operation time contained 7.6% by weight of acetic acid and 0.5% by weight of acrylic acid. Whereas, the fluid extracted from the bottom of the azeotropic separation column 102 through line 15 contained 97.1% by weight of acrylic acid, 0.05% by weight of acetic acid and 2.85% by weight of other miscellaneous components, while containing no more than the detection limit (1 ppm) of the solvent.

When the azeotropic separation column 102 was continuously run for about 14 days under said conditions, steady operating conditions were constantly obtained. When inside of the column was inspected after suspension of the operation, indication of polymer formation was nil.

EXAMPLE 4

Azeotropic distillation of aqueous acrylic acid solution was conducted in identical manner with Example 1, except that a mixed solvent of methyl methacrylate and heptane (blend ratio: 35:65 by weight) was used as the azeotropic solvent and the reflux ratio was decreased to 1.24.

The aqueous phase at line 8 at steady operation time contained 7.3% by weight of acetic acid and 0.6% by weight of acrylic acid. Whereas, the fluid extracted from the bottom of the azeotropic separation column 102 through line 15 contained 97.2% by weight of acrylic acid, 0.04% by weight of acetic acid and 2.76% by weight of other miscellaneous components, while containing no more than the detection limit (1 ppm) of the solvent.

When the azeotropic separation column 102 was continuously run for about 14 days under said conditions, steady operating conditions were constantly obtained. When inside of the column was inspected after suspension of the operation, indication of polymer formation was nil.

EXAMPLE 5

A gaseous mixture obtained by gas-phase catalytic oxidation of propylene with a molecular oxygen-containing gas was led to an acrylic acid collection column and contacted with water. So obtained aqueous solution of acrylic acid was led to an acrolein release column where the acrolein contained in said solution was released. The remaining aqueous acrylic acid solution contained 30% by weight of water and 3.0% by weight of acetic acid. The solution was then distilled in an azeotropic separation column equipped with a sieve tray with 50 plates disposed at regular intervals of 147 mm each, a distillation pipe at the column top, a starting material supply pipe at the center and a bottom product-extracting pipe at the bottom part. As the azeotropic solvent, a mixed solvent of methyl methacrylate and toluene (blend ratio: 35:65 by weight) was used.

As the polymerization inhibitor, 15 ppm of copper dibutyldithiocarbamate and 150 ppm of hydroquinone, each to the amount of evaporated acrylic acid vapor, were used, both of which were added to the column in the form as dissolved in the reflux fluid from the column top. Separately, 0.3% by volume to the vapor of evaporated acrylic acid of molecular oxygen was supplied to the bottom part of the column.

The operating conditions of the azeotropic separation column at the steady operation time were: column top temperature, 47° C.; column bottom temperature, 102° C.; column top pressure, 160 mmHg, reflux ratio (total mol number of reflux fluid per unit time/total mol number of distillate per unit time), 1.17; and the aqueous acrylic acid solution supply, 10.7 liters/hour. The aqueous phase obtained from the column top contained 1.5% by weight of acetic acid and 0.7% by weight of acrylic acid. Whereas, the fluid extracted from the bottom of the column contained 95.1% by weight of acrylic acid, 2.2% by weight of acetic acid and 2.7% by weight of other miscellaneous components.

When the azeotropic separation column was continuously run for about 14 days under said conditions, always stable operation conditions were maintained. When inside of the distillation column was inspected after suspension of the operation, indication of polymer formation was nil.

COMPARATIVE EXAMPLE 4

Azeotropic distillation of aqueous acrylic acid solution was conducted in identical manner with Example 5, except that toluene alone was used as the azeotropic solvent and the reflux ratio was changed to 1.20.

The aqueous phase obtained from the column top at steady operation time contained 4.2% by weight of acetic acid and 0.4% by weight of acrylic acid; and the fluid extracted from the bottom of the column contained 94.1% by weight of acrylic acid, 1.8% by weight of acetic acid and 4.1% by weight of other miscellaneous components.

When the azeotropic separation column was continuously operated under the above-specified conditions, 4 days after the operation had been started a pressure loss within the column was observed, which rendered continuation of the operation difficult. The operation was suspended, therefore, and the column was dismembered and inspected. Whereupon formation of a viscous polymer in the column was recognized.

COMPARATIVE EXAMPLE 5

Azeotropic distillation of aqueous acrylic acid solution was conducted in identical manner with Example 1, except that a mixed solvent of ethyl methacrylate and toluene (blend ratio: 50:50 by weight) was used as the azeotropic solvent and the reflux ratio was reduced to 1.01.

The aqueous phase at line 8 at steady operation time contained 7.0% by weight of acetic acid and 1.3% by weight of acrylic acid, ie., twice as much acrylic acid of that contained in the aqueous phase in Example 1. Whereas, the fluid extracted from the bottom of the azeotropic separation column 102 through line 15 contained 96.5% by weight of acrylic acid, 0.12% by weight of acetic acid, 0.005% by weight of the solvent and 3.38% by weight of other miscellaneous components. Thus, the acetic acid content was higher than that in the product of Example 1 by the order of one figure, and the solvent content was more than 50 times that in Example 1.

As above, when a mixed solvent of ethyl methacrylate containing 6 carbon atoms and toluene was used, acrylic acid of satisfactory quality could not be obtained by single distillation operation.

COMPARATIVE EXAMPLE 6

Azeotropic distillation of aqueous acrylic acid solution was conducted in identical manner with Example 1, except that a mixed solvent of propyl acrylate and heptane (blend ratio: 50:50 by weight) was used as the azeotropic solvent and the reflux ratio was changed to 1.08.

The aqueous phase at line 8 at steady operation time contained 6.7% by weight of acetic acid and 1.5% by weight of acrylic acid, ie., twice as much acrylic acid of that contained in the aqueous phase in Example 1. Whereas, the fluid extracted from the bottom of the azeotropic separation column 102 through line 15 contained 96.3% by weight of acrylic acid, 0.15% by weight of acetic acid, 0.01% by weight of the solvent and 3.54% by weight of other miscellaneous components. Thus, the acetic acid content was higher than that in the product of Example 1 by the order of one figure, and the solvent content was more than 100 times that in Example 1.

As above, when a mixed solvent of propyl acrylate containing 6 carbon atoms and heptane was used, acrylic acid of satisfactory quality could not be obtained by single distillation operation.

EXAMPLE 6

Acrylic acid was recovered following the steps as illustrated in FIG. 2.

A gaseous mixture obtained by gas-phase catalytic oxidation of propylene with a molecular oxygen-containing gas (air) was led to an acrylic acid collection column 201, contacted with water and collected. So collected aqueous solution of acrylic acid was led to an acrolein release column (not shown) where the acrolein contained in said solution was released. The remaining aqueous acrylic acid solution contained 30% by weight of water and 3.0% by weight of acetic acid. The solution was then introduced into an azeotropic separation column 202 equipped with a sieve tray with 50 plates disposed at a regular interval of 147 mm each, a distillation pipe at the column top, a starting material supply pipe at the center and a bottom product-extracting pipe at the bottom part. As the azeotropic solvent, methyl methacrylate was used, and an azeotropic distillation of the aqueous acrylic acid solution was conducted.

The amounts of the polymerization inhibitors used were, to the amount of vapor of evaporated acrylic acid, 15 ppm of copper dibutyidithiocarbamate and 150 ppm of hydroquinone, both of which were supplied into the column in the form dissolved in the reflux fluid from the column top. Separately, 0.3% by volume to the vapor of evaporated acrylic acid of molecular oxygen was supplied to the bottom portion of the column. Here the amount of the evaporated vapor signifies the total volume of the monomer vapor evaporated from the bottom of the column in correspondence to the heat applied from the reboiler of the distillation column.

The operating conditions of the azeotropic separation column 202 at the steady operation time were: column top temperature, 45° C.; column bottom temperature, 99° C.; column top pressure, 160 mmHg, reflux ratio (total mol number of reflux fluid per unit time/total mol number of distillate per unit time), 1.24; and the aqueous acrylic acid solution supply through line 24, 10.2 liters/hour. The aqueous phase obtained from the top of this azeotropic separation column 202 contained 0.2% by weight of acetic acid and 0.6% by weight of acrylic acid. Whereas, the fluid extracted from the bottom of the column contained 94.5% by weight of acrylic acid, 2.8% by weight of acetic acid and 2.7% by weight of other miscellaneous components, while containing no more than the detection limit (1 ppm) of the solvent.

When the azeotropic separation column 202 was continuously run for about 14 days under the specified conditions, steady operating conditions were constantly obtained. When inside of the column was inspected after suspension of the operation, indication of polymer formation was nil.

COMPARATIVE EXAMPLE 7

Azeotropic distillation of aqueous acrylic acid solution was conducted in the identical manner with Example 6, except that n-butyl acetate was used as the azeotropic solvent and the reflux ratio was reduced to 0.39.

The aqueous phase obtained from the top of the azeotropic separation column 202 at steady operation time contained 1.6% by weight of acetic acid and 1.0% by weight of acrylic acid. Whereas, the fluid extracted from the bottom of the column contained 94.4% by weight of acrylic acid, 2.7% by weight of acetic acid, 0.013% by weight of the solvent and 2.9% by weight of other miscellaneous components. Thus, its content of the residual solvent was more than 100 times that in Example 6.

COMPARATIVE EXAMPLE 8

Azeotropic distillation of aqueous acrylic acid solution was conducted in the identical manner with Example 6, except that ethyl methacrylate was used as the azeotropic solvent and the reflux ratio was reduced to 0.58.

The aqueous phase obtained from the top of the azeotropic separation column 202 at steady operation time contained 1.2% by weight of acetic acid and 1.8% by weight of acrylic acid. Whereas, the fluid extracted from the bottom of the column contained 94.7% by weight of acrylic acid, 2.5% by weight of acetic acid, 2 ppm of the solvent and 2.8% by weight of other miscellaneous components. Thus, when separation of the solvent at the azeotropic separation column 202 was attempted, the acetic acid and acrylic acid contents in the distillate became not negligible.

According to the first embodiment of the method of the invention, polymerization of acrylic acid in an azeotropic separation column can be effectively prevented in consequence of using the specified mixed solvent as an azeotropic solvent, which enables continuous operation of the azeotropic separation column over a prolonged period.

Furthermore, according to the first embodiment, high purity acrylic acid which is substantially free of acetic acid can be obtained from the bottom of the azeotropic separation column, through only a single time distillation operation using the specified mixed solvent as azeotropic solvent, in which an aqueous acrylic acid solution containing side-products such as acetic acid is distilled in the azeotropic separation column, distilling off an azeotropic mixture composed of acetic acid, water and the azeotropic solvent from the column top.

According to the second embodiment method of subject invention, high purity acrylic acid which is substantially free of acetic acid can also be obtained through two distillation operations, in which aqueous acrylic acid solution containing side-products such as acetic acid is distilled in an azeotropic separation column to distill off from the column top an azeotropic mixture composed of water and a specified azeotropic solvent or of water, the azeotropic solvent and a part of the acetic acid and to recover from the bottom of the column crude acrylic acid containing the rest of acetic acid; and said crude acrylic acid is led to an acetic acid separation column where the acetic acid is separated by distillation. Because the azeotropic solvent used in the second embodiment method excells in separability and its blending into the acrylic acid obtained from the azeotropic separation column is extremely little, high purity acrylic acid can be prepared according to the method of this embodiment. Employing this embodiment, again polymerization of acrylic acid within the azeotropic separation column can be effectively prevented.

What is claimed is:

1. A method for recovering acrylic acid which comprises contacting an acrylic acid-containing gas, which is obtained upon gas-phase catalytic oxidation of propylene and/or acrolein, with water, whereby collecting the acrylic acid in form of an aqueous solution, and introducing said aqueous acrylic acid solution into an azeotropic separation column and distilling the same in the presence of an azeotropic solvent, whereby isolating and recovering acrylic acid, wherein said azeotropic solvent comprises a mixed solvent blend containing;

at least one solvent A selected from the group consisting of ethyl acrylate, methyl methacrylate, vinyl acrylate, allyl acetate, isopropenyl acetate, vinyl propionate and methyl crotonate; and at least one solvent B selected from the group consisting of toluene, heptane, 1-heptene, methylcyclohexane, cycloheptene, cycloheptadiene, cycloheptatriene, 2,4-dimethyl-1,3-pentadiene, methylcyclohexene and methylenecyclohexane is used as the azeotropic solvent.

2. A method according to claim 1, wherein said solvent A is at least one selected from ethyl acrylate and methyl methacrylate, and said solvent B is at least one selected from toluene and heptane.

3. A method according to claim 1, wherein the blend ratio of the solvent A to solvent B ranges, in terms of weight ratio, is from 10:90 to 75:25.

4. A method according to claim 1, 2, or 3 wherein acetic acid is distilled off from the top of the azeotropic separation column and an acrylic acid which is substantially free of acetic acid is recovered from the bottom of the column.

5. A method for recovering acrylic acid which comprises contacting an acrylic acid-containing gas, which is obtained upon gas-phase catalytic oxidation of propylene and/or acrolein, with water, whereby collecting the acrylic acid in form of an aqueous solution, and introducing said aqueous solution into an azeotropic distillation column and distilling it in the presence of an azeotropic solvent to isolate and recover the acrylic acid, characterized by using as the azeotropic solvent at least one solvent selected from the group consisting of ethyl acrylate, methyl methacrylate, vinyl acrylate, allyl acetate, isopropenyl acetate, vinyl propionate and methyl crotonate.

6. A method according to claim 5, wherein the acrylic acid extracted from the azeotropic separation column is further purified in an acetic acid separation column.

7. A method according to claim 5 or 6, wherein the azeotropic solvent is methyl methacrylate.

8. The method according to claim 2, wherein the blend ratio of the solvent A to solvent B ranges, in terms of weight ratio, is from 10:90 to 75:25.

9. A method for recovering acrylic acid which comprises contacting an acrylic acid-containing gas, which is obtained upon gas-phase catalytic oxidation of propylene and/or acrolein, with water, whereby collecting the acrylic acid in form of an aqueous solution, and introduction said aqueous acrylic acid solution into an azeotropic separation column and distilling the same in the presence of an azeotropic solvent, wherein said azeotropic solvent comprises a mixed solvent blend containing;

at least one solvent A selected from the group consisting of ethyl acrylate and methyl methacrylate; and at least one solvent B selected from the group consisting of toluene and heptane is used as the azeotropic solvent, wherein the blend ratio of the solvent A to solvent B ranges, in terms of weight ratio, is from 20:80 to 50:50; and the acetic acid is distilled off from the top of the azeotropic separation column and an acrylic acid which is substantially free of acetic acid is recovered from the bottom of the column.

10. The method of claim 1 wherein the acrylic acid recovered from the bottom of the column contains 0.05% by weight or less of acetic acid, and 1 ppm or less of the solvent.

11. A method for recovering acrylic acid which comprises contacting an acrylic acid-containing gas, which is obtained upon gas-phase catalytic oxidation of propylene and/or acrolein, with water, whereby collecting the acrylic acid in form of an aqueous solution, and introduction said aqueous acrylic acid solution into an azeotropic separation column and distilling the same in the presence of an azeotropic solvent, wherein said azeotropic solvent comprises a mixed solvent blend containing;

at least one solvent A selected from the group consisting of ethyl acrylate and methyl methacrylate; and at least one solvent B selected from the group consisting of toluene and heptane is used as the azeotropic solvent, wherein the blend ratio of the solvent A to solvent B ranges, in terms of weight ratio, is from 20:80 to 50:50; and the acetic acid is distilled off from the top of the azeotropic separation column and acrylic acid which contains 0.05% by weight or less of acetic acid, and 1 ppm or less of the solvent is recovered from the bottom of the column.

\* \* \* \* \*